US009103799B2

(12) United States Patent
Andoh et al.

(10) Patent No.: US 9,103,799 B2
(45) Date of Patent: Aug. 11, 2015

(54) METHOD FOR MONITORING GLASS MELTING FURNACE, METHOD FOR CONTROLLING INTRODUCTION OF RAW MATERIAL, AND DEVICE FOR CONTROLLING INTRODUCTION OF RAW MATERIAL

(75) Inventors: Michihiro Andoh, Hyogo (JP); Shuichi Yadori, Hyogo (JP)

(73) Assignee: NIHON YAMAMURA GLASS CO., LTD., Hyogo (JP)

(*) Notice: Subject to any disclaimer, the term of this patent is extended or adjusted under 35 U.S.C. 154(b) by 272 days.

(21) Appl. No.: 13/575,129

(22) PCT Filed: Feb. 16, 2011

(86) PCT No.: PCT/JP2011/053292
§ 371 (c)(1),
(2), (4) Date: Jul. 25, 2012

(87) PCT Pub. No.: WO2011/102391
PCT Pub. Date: Aug. 25, 2011

(65) Prior Publication Data
US 2012/0291489 A1    Nov. 22, 2012

(30) Foreign Application Priority Data
Feb. 19, 2010 (JP) ................................ 2010-035356

(51) Int. Cl.
*C03B 3/00* (2006.01)
*C03B 5/24* (2006.01)
*G01N 21/85* (2006.01)

(52) U.S. Cl.
CPC *G01N 21/85* (2013.01); *C03B 3/00* (2013.01); *C03B 5/245* (2013.01)

(58) Field of Classification Search
CPC ............ C03B 7/005; C03B 5/24; C03B 5/04; C03B 2211/00; C03B 3/00; C03B 5/0336; C03B 5/06; C03B 5/08; C03B 5/42; C03B 5/44
USPC ....................... 65/158, 160, 134.1, 29.16, 335
See application file for complete search history.

(56) References Cited

U.S. PATENT DOCUMENTS 4,409,012 A * 10/1983 Miller ........................ 65/29.18
5,328,495 A *  7/1994 Okafuji et al. ................. 65/99.5
(Continued)

FOREIGN PATENT DOCUMENTS

JP    53-045316 A    4/1978
JP    58-142224 A    8/1983
(Continued)

*Primary Examiner* — Jodi C Franklin
(74) *Attorney, Agent, or Firm* — Rabin & Berdo, P.C.

(57) ABSTRACT

Method for monitoring molten state of a glass batch charged into a melting bath of a glass melting furnace, and a method and control device for controlling an amount of a glass batch to be so charged. Regions to be measured are set in regions corresponding to particular partial regions on an image obtained by capturing an image of a liquid surface of the bath to be monitored using a camera. The occupying ratio of an area occupied by image portions representing unmolten glass batches in each region, and a distribution state of the batches in the partial region is recognized from the measured value of the occupying ratios so as to determine whether the molten state quality of the batch is favorable. When the determined quality is not favorable, the amounts thereof to be charged by batch chargers are controlled so that appropriate distribution states can be obtained.

8 Claims, 13 Drawing Sheets

(56) References Cited

U.S. PATENT DOCUMENTS

| | | | |
|---|---|---|---|
| 6,796,147 B2* | 9/2004 | Borysowicz et al. | 65/162 |
| 2004/0079113 A1* | 4/2004 | Hegewald et al. | 65/29.16 |
| 2010/0251772 A1* | 10/2010 | Itoh et al. | 65/32.1 |
| 2012/0137737 A1* | 6/2012 | Sakamoto et al. | 65/66 |

FOREIGN PATENT DOCUMENTS

| | | |
|---|---|---|
| JP | 61-183126 A | 8/1986 |
| JP | H1-122041 U | 8/1989 |
| JP | 2009-161396 A | 7/2009 |

\* cited by examiner

METHOD FOR MONITORING GLASS MELTING FURNACE, METHOD FOR CONTROLLING INTRODUCTION OF RAW MATERIAL, AND DEVICE FOR CONTROLLING INTRODUCTION OF RAW MATERIAL

FIELD

The present invention relates to a glass melting furnace for producing molten glass to be supplied to a glass product forming machine such as a bottle making machine. In particular, the present invention relates to a glass melting furnace monitoring method for monitoring a molten state of a glass batch charged into a melting bath of a glass melting furnace by a batch charger, a glass melting furnace batch charging control method for controlling an amount of the glass batch to be charged into the melting bath of the glass melting furnace by the batch charger, and a device for controlling batch charging in a glass melting furnace used to implement the batch charging control method.

BACKGROUND

A conventional glass melting furnace shown in FIG. 13 includes: a batch introducing port 101 for introducing a glass batch into a melting bath 100 in the furnace; a plurality of combustion ports 102 respectively communicated with combustion burners not shown in the figure; and a derivation port 103 for introducing molten glass out from the melting bath 100. At a position outside the furnace corresponding to the batch introducing port 101, a batch charger 104 is placed for charging a glass batch into the melting bath 100 from the batch introducing port 101 (see Patent Literature 1, for example).

In another conventional glass melting furnace shown in FIG. 14, the batch introducing ports 101, 101 and the combustion ports 102, 102 are provided at horizontally symmetrical positions, respectively, in an upstream region of the melting bath 100, and the batch chargers 104 are provided at positions outside the furnace corresponding to the batch introducing ports 101, respectively.

In each of the above-described glass melting furnaces, an image-capturing device 105 is provided at a position above a downstream region of the melting bath 100. The image-capturing device 105 is to capture an image of an entire liquid surface of the molten glass filled in the melting bath 100 from an obliquely upward position, and the image obtained at the image-capturing device 105 is shown on a monitoring television 106. An operator manually adjusts the amount of the glass batch to be charged by the batch charger 104 while looking at the image on the monitoring television 106 to monitor the charging state of the glass batch into the melting bath 100.

CITATION LIST

Patent Literature

Patent Literature 1: Japanese Patent Application Laid-Open No. Sho. 61-183126

SUMMARY

Technical Problem

According to the above-described glass melting furnaces, an operator manually adjusts the amount of the glass batch to be charged by the batch charger 104 while looking at the image on the monitoring television 106 to monitor the charging state of the glass batch into the melting bath 100 by the batch charger and the molten state of the glass batch. Thus, not only a workload for the operator is large, but also it is difficult to optimally adjust the charging amount of the glass batch since a skill is required to determine whether the charging amount of the glass batch is appropriate or not.

Moreover, according to the glass melting furnace shown in FIG. 14, the charging amount of the glass batch to be made by each of the batch chargers 104 needs to be adjusted individually. This type of adjusting operation is not easy, and there are risks such that a judgment error, an adjustment error, a delayed adjustment timing, or the like leads to an inhomogeneous distribution of unmolten glass batches and thus to unevenness in the molten glass, thereby resulting in the instability of the glass product quality and the generation of defects.

The present invention has been made in view of the above-described problems and an object thereof is to provide a method for monitoring a glass melting furnace capable of determining whether the quality of the molten state of the glass batch is favorable or not utilizing an image processing technique without depending on a skilled operator, and optimally adjusting the charging amount of the glass batch by monitoring the molten state of the glass batch charged into the melting bath of the glass melting furnace by the batch charger on the basis of the distribution state of the unmolten glass batches in a particular partial region.

Moreover, another object of the present invention is to provide a method and a device for controlling batch charging in a glass melting furnace, capable of preventing the occurrence of unevenness in the molten glass and therefore eliminating risks of making the quality of glass products unstable and generating defects by controlling the amount of the glass batch to be charged into the melting bath by the batch charger so as to obtain an appropriate distribution state of the unmolten glass batches on the basis of the determination that the quality of the molten state of the glass batch is not favorable.

Solution to Problem

A method for monitoring a glass melting furnace according to the present invention is a method for monitoring a molten state of a glass batch charged into a melting bath of a glass melting furnace by a batch charger on the basis of a distribution state of unmolten glass batches in a particular partial region, the method including: setting a region to be measured in a region corresponding to the partial region on an image obtained by capturing an image of a liquid surface of the melting bath; measuring an occupying ratio of an area occupied by image portions representing unmolten glass batches in the region to be measured; and recognizing a distribution state of the unmolten glass batches in the partial region from the measured value and determining whether a quality of the molten state of the glass batch is favorable or not.

In a preferred embodiment of the present invention, the batch charger charges the glass batch into an upstream region of the melting bath; the regions to be measured are set respectively in respective partial regions at horizontally symmetrical positions in a region corresponding to the upstream region on the image; respective occupying ratios of areas occupied by image portions representing unmolten glass batches in the respective regions to be measured are measured; and distribution states of the unmolten glass batches in the respective partial regions are recognized from a difference between measured values of the occupied ratios.

In a case where unmolten glass batches called "batch piles" exist respectively in the partial regions at the horizontally symmetrical positions in the upstream region of the melting bath, a distribution amount of the unmolten glass batches in each of the partial regions is reflected by an occupying ratio of an area occupied by image portions representing the unmolten glass batches within each of the regions to be measured on the image. Thus, it is possible to determine whether the quality of the molten state of the glass batch is favorable or not, which is attributed to whether the amount of the glass batch charged into each of the partial regions by the batch charger is appropriate or not, by recognizing a distribution state, i.e., a degree of distribution unevenness, of the unmolten glass batches in each of the partial regions from a difference between the measured values of the occupying ratios of the areas in the regions to be measured. Accordingly, without depending on a skilled operator, it is possible to determine whether the quality of the molten state of the glass batch is favorable or not and to optimally adjust the charging amount of the glass batch by the batch charger.

In another preferred embodiment of the present invention, the batch charger charges a glass batch into divided regions in an upstream region of the melting bath; the region to be measured is set in a region corresponding to any one of the divided partial regions on the image; an occupying ratio of an area occupied by image portions representing unmolten glass batches in the region to be measured is measured; and a distribution state of the unmolten glass batches in the partial region is recognized from a measured value of the occupied ratio.

In a case where unmolten glass batches exist respectively in the partial regions in the upstream region of the melting bath, a distribution amount of the unmolten glass batches in each of the partial regions is reflected by the occupying ratio of the area occupied by the image portions representing the unmolten glass batches within each of the regions to be measured on the image. Thus, it is possible to determine whether the quality of the molten state of the glass batch is favorable or not, which is attributed to whether the amount of the glass batch charged into the partial region by the batch charger is appropriate or not, by recognizing a distribution state of the unmolten glass batches, i.e., a distributed state of glass batches, in the partial region from the measured value of the occupying ratio of the area in the region to be measured. Accordingly, it is possible to determine whether the quality of the molten state of the glass batch is favorable or not without depending on a skilled operator, and to optimally adjust the charging amount of the glass batch by the batch charger.

In yet another preferred embodiment of the present invention, the batch charger charges a glass batch into an upstream region of the melting bath; the region to be measured is set in a partial region within a region corresponding to a downstream region on the image; an occupying ratio of an area occupied by image portions representing unmolten glass batches in the region to be measured is measured; and a distribution state of the unmolten glass batches in the partial region is recognized from a measured value of the occupied ratio.

In a case where unmolten glass batches exist in the partial region within the downstream region of the melting bath, a distribution amount of the unmolten glass batches in the partial region is reflected by the occupying ratio of the area occupied by the image portions representing the unmolten glass batches within the region to be measured on the image. Thus, it is possible to determine whether the quality of the molten state of the glass batch is favorable or not, which is attributed to various factors, by recognizing a distribution state of the unmolten glass batches, i.e., a degree of traveling down of the unmolten glass batches in the partial region from the measured value of the occupying ratio of the area. Accordingly, it is possible to determine whether the quality of the molten state of the glass batch is favorable or not without depending on a skilled operator, and to take an optimal countermeasure.

In a preferred embodiment, when it is determined that a quality of a molten state of a glass batch is not favorable on the basis of a distribution state of unmolten glass batches in a partial region by performing any one of the above-described monitoring methods, an alarm is actuated to inform a situation thereof.

According to this embodiment, the actuation of the alarm makes an operator find out that the quality of the molten state of the glass batch is not favorable and it is therefore necessary to take a countermeasure such as an inspection or operational adjustment of the combustion burner or the batch charger.

According to a glass melting furnace batch charging control method of the present invention, when it is determined that a quality of a molten state of a glass batch is not favorable on the basis of a distribution state of unmolten glass batches by performing any one of the above-described monitoring methods, an amount of the glass batch to be charged into a melting bath by a batch charger is controlled so that an appropriate distribution state can be obtained.

According to this invention, no unevenness occurs in the molten glass in the melting bath, and it is thus possible to eliminate risks of making the quality of glass products manufactured by the molten glass unstable and generating defects.

A glass melting furnace batch charging control device according to the present invention is a device for controlling a charging amount of a glass batch on the basis of a determination result for a molten state of a glass batch charged into a melting bath of the glass melting furnace by a batch charger determined on the basis of a distribution state of unmolten glass batches in a particular partial region, the device including: image-capturing means for capturing an image of a liquid surface of the melting bath from a position above the melting bath; area measuring means for setting a region to be measured in a region corresponding to the partial region on an image obtained by the image-capturing means and measuring an occupying ratio of an area occupied by image portions representing unmolten glass batches in the region to be measured; determination means for recognizing a distribution state of the unmolten glass batches in the partial region from a measured value obtained by the area measuring means and determining whether a quality of the molten state of the glass batch is favorable or not; and control means for controlling an amount of the glass batch to be charged into the melting bath by the batch charger on the basis of the determination result made by the determination means.

According to the glass melting furnace batch charging control device described above, after the image of the liquid surface of the melting bath is captured by the image-capturing means from the position above the melting bath, the region to be measured is set in the region corresponding to the partial region on the image obtained by the image-capturing means and the area measuring means measures the occupying ratio of the area occupied by the image portions representing the unmolten glass batches in the region to be measured. The determination means recognizes the distribution state of the unmolten glass batches in the partial region from the measured value obtained by the area measuring means, and determines whether the quality of the molten state of the glass batch is favorable or not. The control means controls the amount of the glass batch to be charged by the batch charger on the basis of the determination result made by the determination means.

In a preferred embodiment of the present invention, the batch chargers are provided at horizontally symmetrical positions on both sides of an upstream region of the melting bath, respectively. The area measuring means sets the regions to be measured respectively in respective partial regions at horizontally symmetrical positions in a region corresponding to the upstream region on the image, and measures respective occupying ratios of areas occupied by image portions representing unmolten glass batches in the regions to be measured. The determination means recognizes distribution states of the unmolten glass batches in the respective partial regions from a difference between measured values obtained by the area measuring means, and determines whether the quality of the molten state of the glass batch is favorable or not.

According to the glass melting furnace batch charging control device of the embodiment above, the batch chargers charge the glass batch into the melting bath from the horizontally symmetrical positions on both sides of the upstream region of the melting bath. After the image of the liquid surface of the melting bath is captured by the image-capturing means from the position above the melting bath, the regions to be measured are respectively set in the respective partial regions at the horizontally symmetrical positions in the region corresponding to the upstream region on the image. After the occupying ratios of the areas occupied by the image portions representing the unmolten glass batches in the regions to be measured are measured respectively, the distribution states of the unmolten glass batches in the respective partial regions are recognized from a difference between the measured values, and it is then determined whether the quality of the molten state of the glass batch is favorable or not, which is attributed to whether the amounts of the glass batch charged into the melting bath by the batch chargers are appropriate or not.

There exist various methods for the determination means to determine whether the quality of the molten state of the glass batch is favorable or not, which is attributed to whether the charging amount of the glass batch is appropriate or not. According to one preferred embodiment, however, a difference between the occupying ratios of the areas occupied by the image portions representing the unmolten glass batches in the respective regions to be measured is compared with a threshold to recognize the distribution states of the unmolten glass batches in the respective partial regions and thereby determine whether the quality of the molten state of the glass batch is favorable or not, and the control means changes a ratio of the charging amounts of the glass batch by the left and right batch chargers when the determination means makes a determination that the quality of the molten state is not favorable.

In another preferred embodiment of the present invention, the batch charger is provided so that it can charge a glass batch into divided regions in an upstream region of the melting bath. The area measuring means sets a region to be measured in a region corresponding to anyone of the divided partial regions on the image, and measures an occupying ratio of an area occupied by image portions representing unmolten glass batches in the region to be measured. The determination means recognizes a distribution state of the unmolten glass batches in the partial region from a measured value obtained by the area measuring means, and determines whether the quality of the molten state of the glass batch is favorable or not.

According to the glass melting furnace batch charging control device of the embodiment above, the batch charger charges a glass batch into the divided regions in the upstream region of the melting bath. After the image of the liquid surface of the melting bath is captured by the image-capturing means from the position above the melting bath, the region to be measured is set in the region corresponding to any one of the divided partial regions on the image obtained by the image-capturing means. After the occupying ratio of the area occupied by the image portions representing the unmolten glass batches in the region to be measured is measured, the distribution state of the unmolten glass batches in the partial region is recognized from the measured value, and it is then determined whether the quality of the molten state of the glass batch is favorable or not, which is attributed to whether the amount of the glass batch charged into the melting bath by the batch charger is appropriate or not.

There exist various methods for the determination means to determine whether the respective amounts of the glass batch charged in the batch charging directions are appropriate or not. According to one preferred embodiment, however, the occupying ratio of the area occupied by the image portions representing the unmolten glass batches in the region to be measured is compared with a threshold to recognize the distribution state of the glass batch in the partial region and thereby determine whether the quality of the molten state of the glass batch is favorable or not, and the control means controls the amount of the glass batch to be charged into each of the partial regions by the batch charger when the determination means makes a determination that the quality of the molten state is not favorable.

Advantageous Effects of Invention

According to the present invention, the molten state of the glass batch charged into the melting bath of the glass melting furnace by the batch charger is monitored on the basis of the distribution state of the unmolten glass batches in the particular partial region. Thus, it is possible to determine whether the quality of the molten state of the glass batch is favorable or not utilizing the image processing technique without depending on a skilled operator, and to optimally adjust the charging amount of the glass batch. Accordingly, a workload for an operator can be reduced.

Moreover, on the basis of a determination that the quality of the molten state of the glass batch is not favorable, the amount of the glass batch to be charged into the melting bath by the batch charger is controlled so that an appropriate distribution state of the unmolten glass batches can be obtained. It is therefore possible to prevent the occurrence of unevenness in the molten glass in the melting bath, the instability of the glass product quality, the generation of defects, and the like.

DESCRIPTION OF EMBODIMENTS

Figure 1:
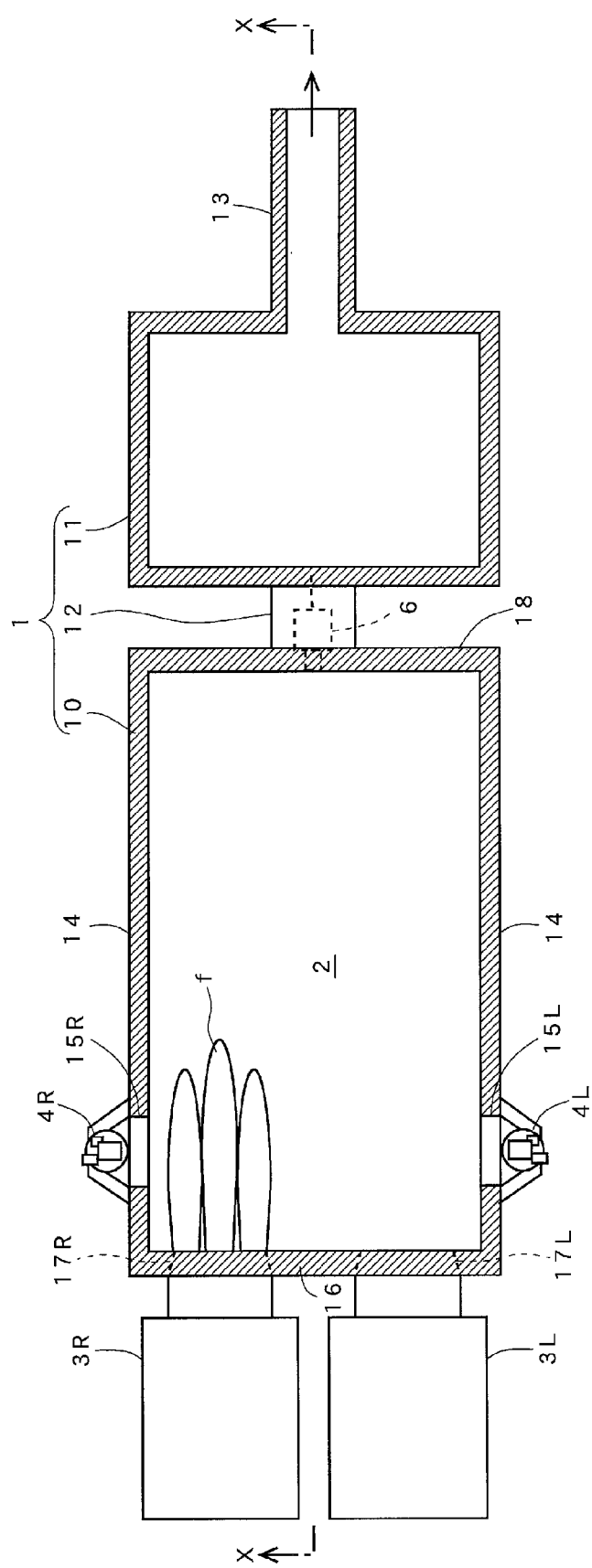
FIG. 1 is a horizontal cross-sectional view of a glass melting furnace according to an embodiment.
Figure 2:
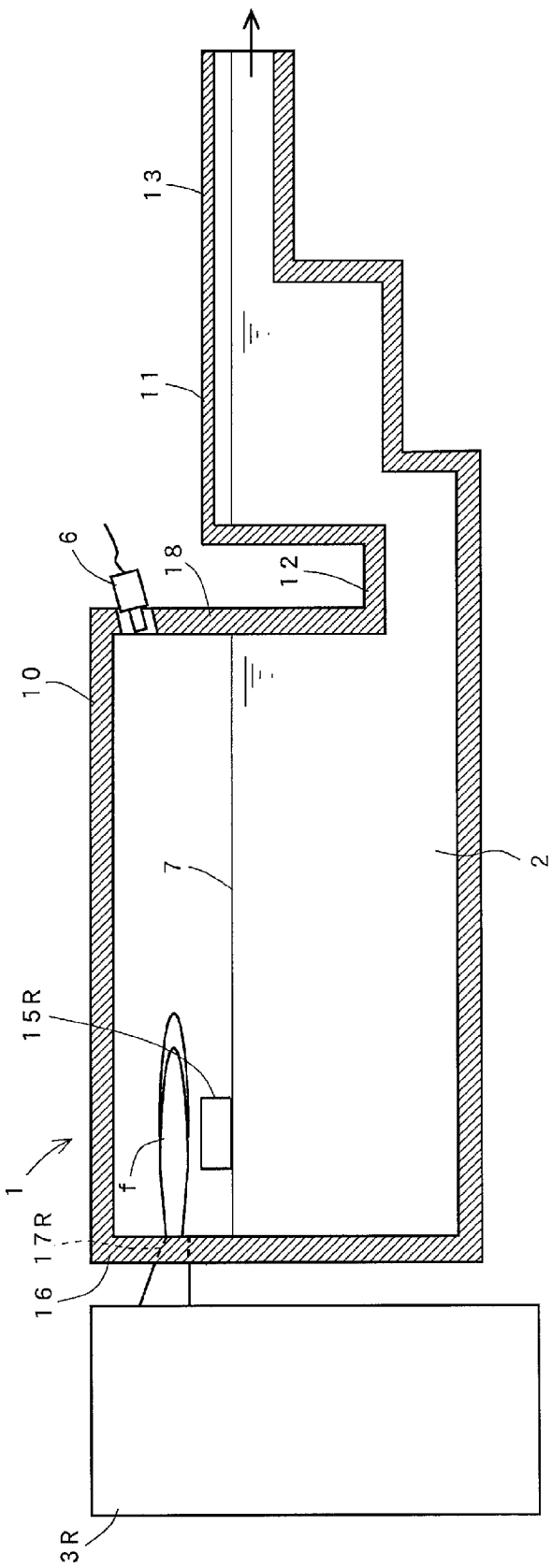
FIG. 2 is a cross-sectional view taken along the line X-X in FIG. 1.

FIGS. 1 and 2 show the configuration of a glass melting furnace 1 to which the present invention is applied. The glass melting furnace 1 exemplified in the figures includes furnace walls formed by a heat insulating material such as fire bricks. The glass melting furnace 1 includes a melting section 10 for heating and melting a glass batch, and a clarifying section 11 for temporarily retaining and clarifying molten glass flowed thereto from the melting section 10 via a communication passage 12. The molten glass retained in the clarifying section 11 is sent to a bottle making machine through an outflow passage 13.

Provided to the melting section 10 are a melting bath 2 for melting a glass batch and retaining the obtained molten glass; a pair of batch introducing ports 15L and 15R provided at symmetrical positions on left and right side walls 14 of the melting section 10 for introducing the glass batch into the melting bath 2; and a pair of combustion ports 17L and 17R provided at horizontally symmetrical positions on a front wall 16 of the melting section 10 for introducing combustion flame f of a pair of combustion burners 3L and 3R into the furnace and introducing exhaust gas out from the furnace. In this embodiment, in order to efficiently utilize a combustion heat, if the combustion flame f is introduced out from one of the combustion ports 17L and 17R, exhaust gas is collected from the other one of the combustion ports 17L and 17R and the recovered heat of the gas is used to preheat combustion air.

Batch chargers 4L and 4R for charging the glass batch into an upstream region of the melting bath 2, i.e., a region closer to the front wall 16, from the respective batch introducing ports 15L and 15R are placed at positions outside the furnace corresponding to the batch introducing ports 15L and 15R. An image-capturing device 6 for capturing an image of a liquid surface 7 of the molten glass filled in the melting bath 2 from an obliquely upward position is placed at an upper position on a back wall 18 of the melting bath 2. Video signals outputted from the image-capturing device 6 are sent to a monitoring television 60 to be described later so that a color video is displayed thereon, and still images obtained by the video signals are loaded into an image processing device 61. Note that the image to be obtained is not limited to a color image, and it may be a monochrome image. An operator can check a molten state and a charging state of the glass batch into the melting bath 2 from a screen of the monitoring television 60.

Figure 3:
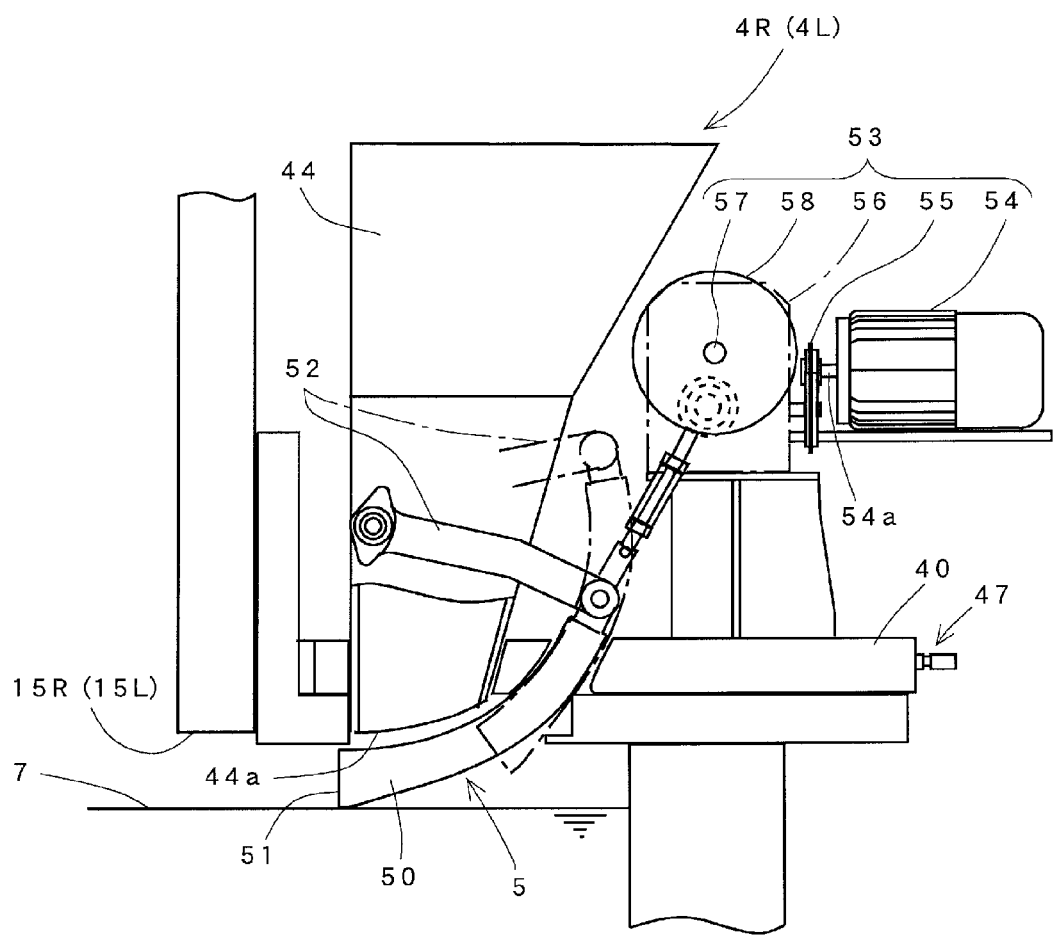
FIG. 3 is an elevation view showing the configuration of a batch charger.
Figure 4:
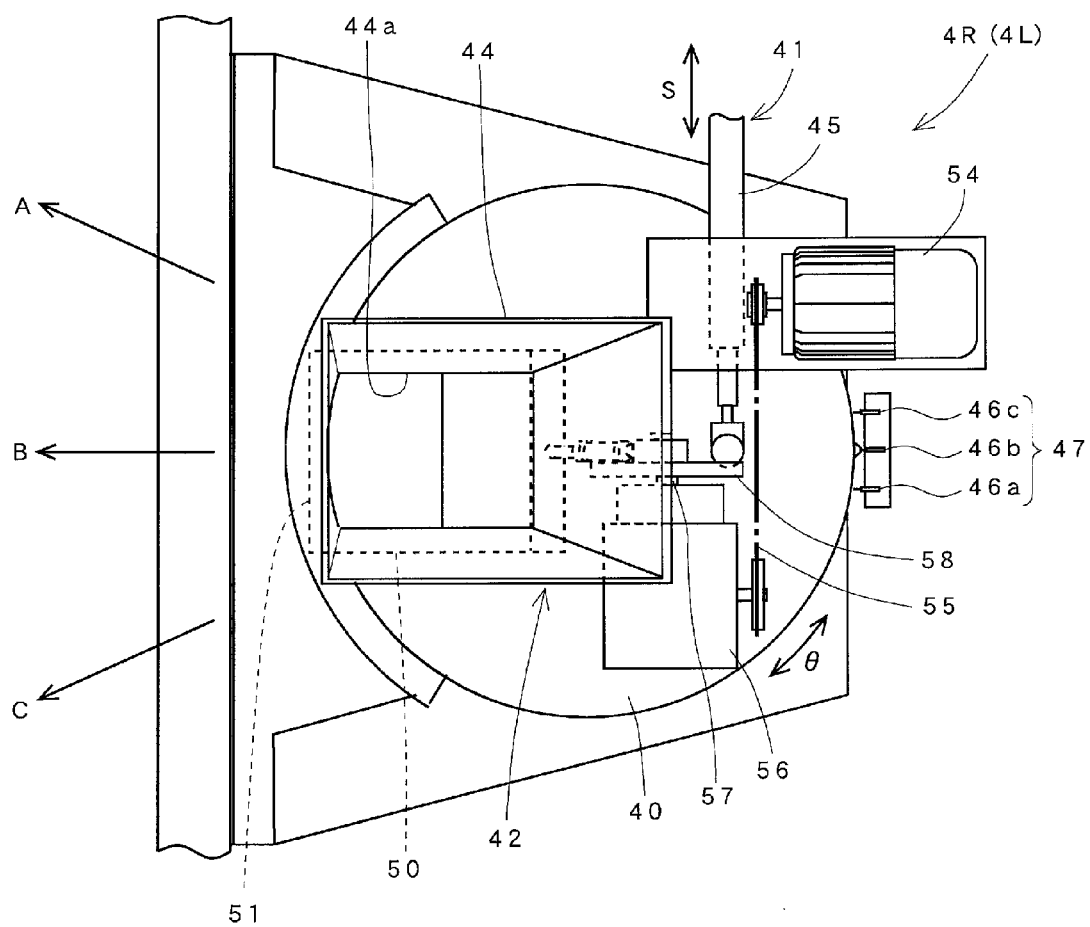
FIG. 4 is a plan view showing the configuration of the batch charger.

Although FIGS. 3 and 4 show a specific configuration of the respective batch chargers 4L and 4R used in the present embodiment, it is to be understood that the respective batch chargers 4L and 4R are not limited to those of the present embodiment. The batch chargers 4L and 4R exemplified in the figures each include: a rotating table 40 horizontally supported so as to be rotatable in forward and reverse directions; a swing motion mechanism 41 for making the rotating table 40 swing over a certain angular range θ and stop at a predetermined angular position for a predetermined amount of time; and a batch feeding mechanism 42 mounted on the rotating table 40 for feeding the glass batch into the melting bath 2 from the batch introducing port 15L or 15R.

The batch feeding mechanism 42 includes a hopper 44 for receiving and temporarily retaining the glass batch supplied from an electromagnetic feeder 43 not shown in these figures (shown in a block diagram of FIG. 10 to be described later); and a pusher mechanism 5 for pushing out the glass batch discharged from a batch discharging port 44a provided at a lower end of the hopper 44 into the melting bath 2 from the batch introducing port 15L or 15R.

The pusher mechanism 5 has a pusher 50 for reciprocating at a certain stroke below the batch discharging port 44a of the hopper 44. The pusher 50 has a plate-like body of a curved shape, and has a pushing face 51 at a front edge face thereof for pushing out the glass batch forward. A base end portion of the pusher 50 is supported by support arms 52, 52 provided at both right and left sides thereof so as to be capable of reciprocating, and is connected to a pusher drive mechanism 53.

The pusher drive mechanism 53 includes: a pusher motor 54 serving as a driving source; a gear reducing mechanism 56 connected to a motor shaft 54a of the pusher motor 54 via a power transmission mechanism 55 such as a transmission belt; and a power conversion mechanism 58 connected to an output shaft 57 of the gear reducing mechanism 56 for converting a rotational motion to a reciprocating motion to be transmitted to the pusher 50. A charging amount of the glass batch into the melting bath 2 is proportional to the number of reciprocating motions (reciprocation speed) of the pusher 50 per unit time, and the number of reciprocating motions is determined by the rotational speed (the number of rotations) of the pusher motor 54. Although a charging amount of the glass batch is adjusted by changing the rotational speed of the motor 54 in this embodiment, it may be adjusted by changing a frequency of the electromagnetic feeder 43.

The swing motion mechanism 41 uses a swing motion motor not shown in the figure as a driving source. The swing motion mechanism 41 allows a rod 45 to reciprocate by a certain distance S in accordance with the rotation of the swing motion motor and allows the rotating table 40 to swing in the forward and reverse directions over the certain angular range θ. In order to make the rotating table 40 stop at predetermined three angular positions, an angular position detector 47 composed of three limit switches 46a, 46b, and 46c are provided along the periphery of the rotating table 40.

At an angular position where the central limit switch 46b of the three limit switches is turned ON, the batch charging direction by the pusher 50 corresponds to a direction shown by B in the figure. At an angular position where the limit switch 46a at one end is turned ON, the batch charging direction by the pusher 50 corresponds to a direction shown by A in the figure. At an angular position where the limit switch 46c at the other end is turned ON, the batch charging direction by the pusher 50 corresponds to a direction shown by C in the figure.

In this embodiment, in order to allow the glass batch to be charged into divided regions in the upstream region of the melting bath 2, the batch feeding mechanisms 42 of the batch chargers 4L and 4R are made to perform swing motions so as to change the batch charging direction thereof. However, the present invention is not limited thereto, and the batch may be charged in a fixed direction without allowing the swing motions.

Figure 5:
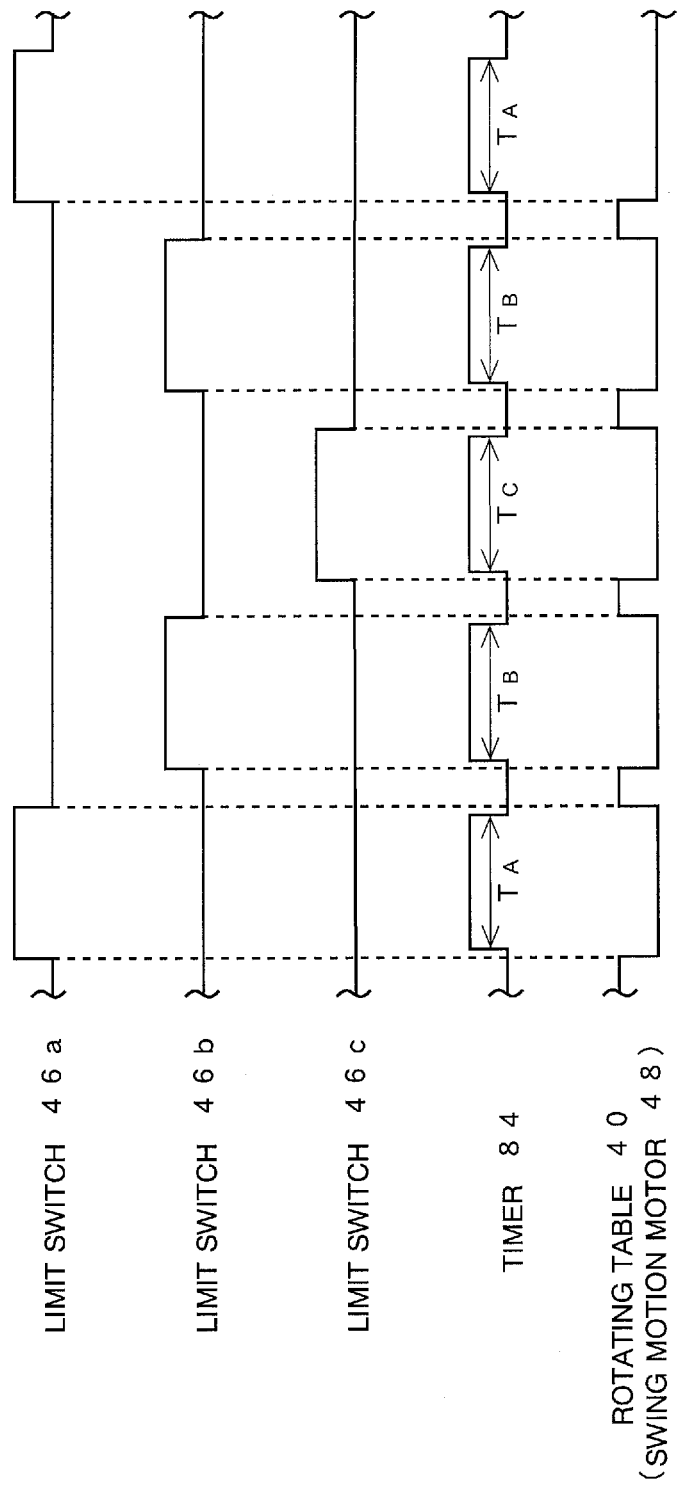
FIG. 5 is a timing chart for swing motions of the batch charger.

As shown in FIG. 5, every time each of the limit switches 46a to 46c is turned ON, the driving of a swing motion motor 48 is stopped so that the swing motion of the rotating table 40 is stopped and placed at an assigned position. During this period, the pusher 50 reciprocates so as to charge the glass batch into the melting bath 2. The charging amounts (distribution amounts) of the glass batch in the batch charging directions A to C are respectively determined by the number of reciprocating motions by the pusher 50 during swing motion stop periods $T_A$ to $T_C$. Thus, if the reciprocation speed of the pusher 50 is constant, the charging amounts are proportional to time lengths of the swing motion stop periods $T_A$ to $T_C$. The swing motion stop periods $T_A$ to $T_C$ are set in a timer 84 to be described later (shown in the timing chart of FIG. 5 and the block diagram of FIG. 10) and timed.

A batch charging period T during which the batch chargers 4L and 4R make one reciprocating motion over the certain angular range θ is equal to $T_A+2T_B+T_C$. The batch charging period T is set constant, and the number of rotations of the pusher motor 54 is changed on the basis of a detection signal from a liquid surface sensor S2 to change the charging amount (total amount) of the glass batch. The swing motion stop periods $T_A$ to $T_C$ are changed according to a second method to be described later to change the charging amounts (distribution amounts) of the glass batch in the respective batch charging directions A to C.

Note that the glass melting furnace 1 to which the present invention is applied is not limited to that having the configuration of FIG. 1, and it may have a batch introducing port only at one of the left and right positions. Alternatively, it may have a configuration in which a plurality of batch chargers 4 are arranged side by side as shown in FIG. 6.

Figure 6:
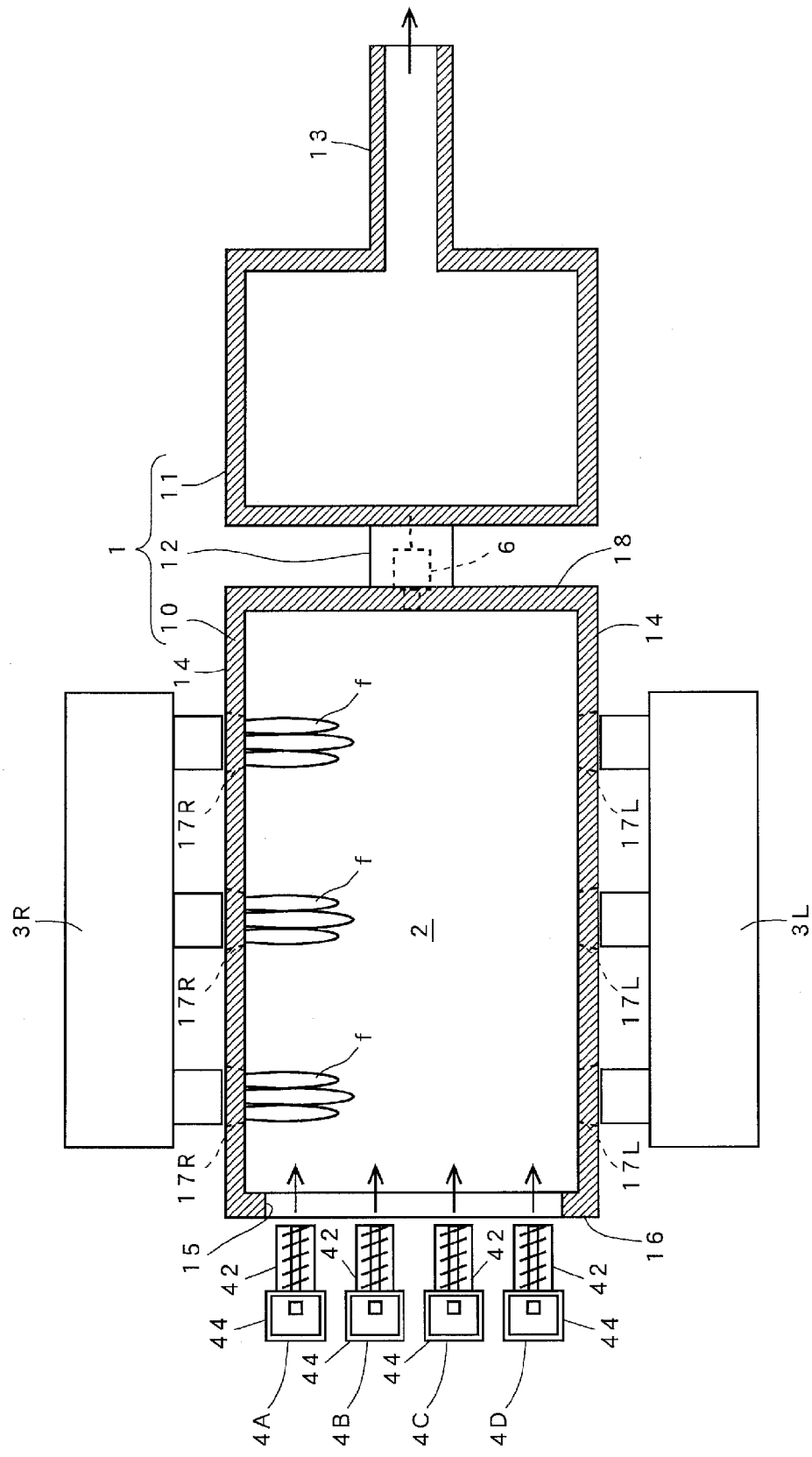
FIG. 6 is a horizontal cross-sectional view of a glass melting furnace according to another embodiment.

The glass melting furnace 1 of FIG. 6 includes: the batch introducing port 15 provided at the front wall 16 of the melting section 10 for introducing the glass batch into the melting bath 2; and the combustion ports 17L and 17R provided at the left and right side walls 14, 14 for introducing combustion flame of the combustion burners 3L and 3R into the furnace and introducing exhaust gas out from the furnace. A plurality of batch chargers 4A to 4D for charging the glass batch into divided regions at the upstream position of the melting bath 2 from the batch introducing port 15 are placed side by side at a position outside the furnace corresponding to the batch introducing port 15.

In the respective batch chargers 4A to 4D exemplified in the figure, the batch feeding mechanisms 42 are configured with screw feeders, respectively, and the glass batches fed from the hoppers 44 are simultaneously sent out into different regions in the same directions (directions shown by arrows) by the batch feeding mechanisms 42. The charging amount (total amount and distribution amount) of the glass batch by each batch charger 4 can be adjusted by the number of rotations of the screw thereof.

Figure 7:
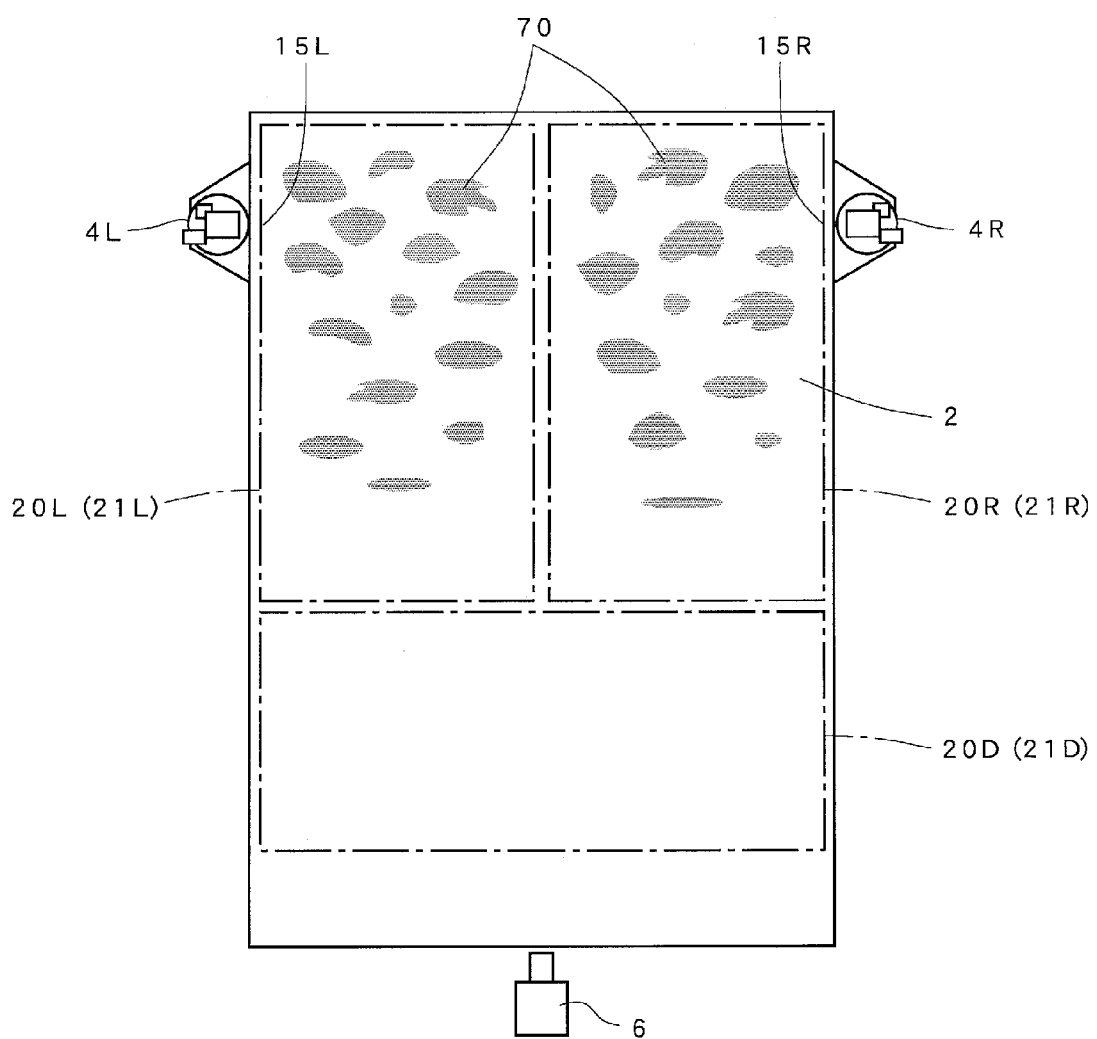
FIG. 7 is an explanatory diagram showing monitored regions on a liquid surface of a melting bath and regions to be measured on an image in an overlapping manner.
Figure 8:
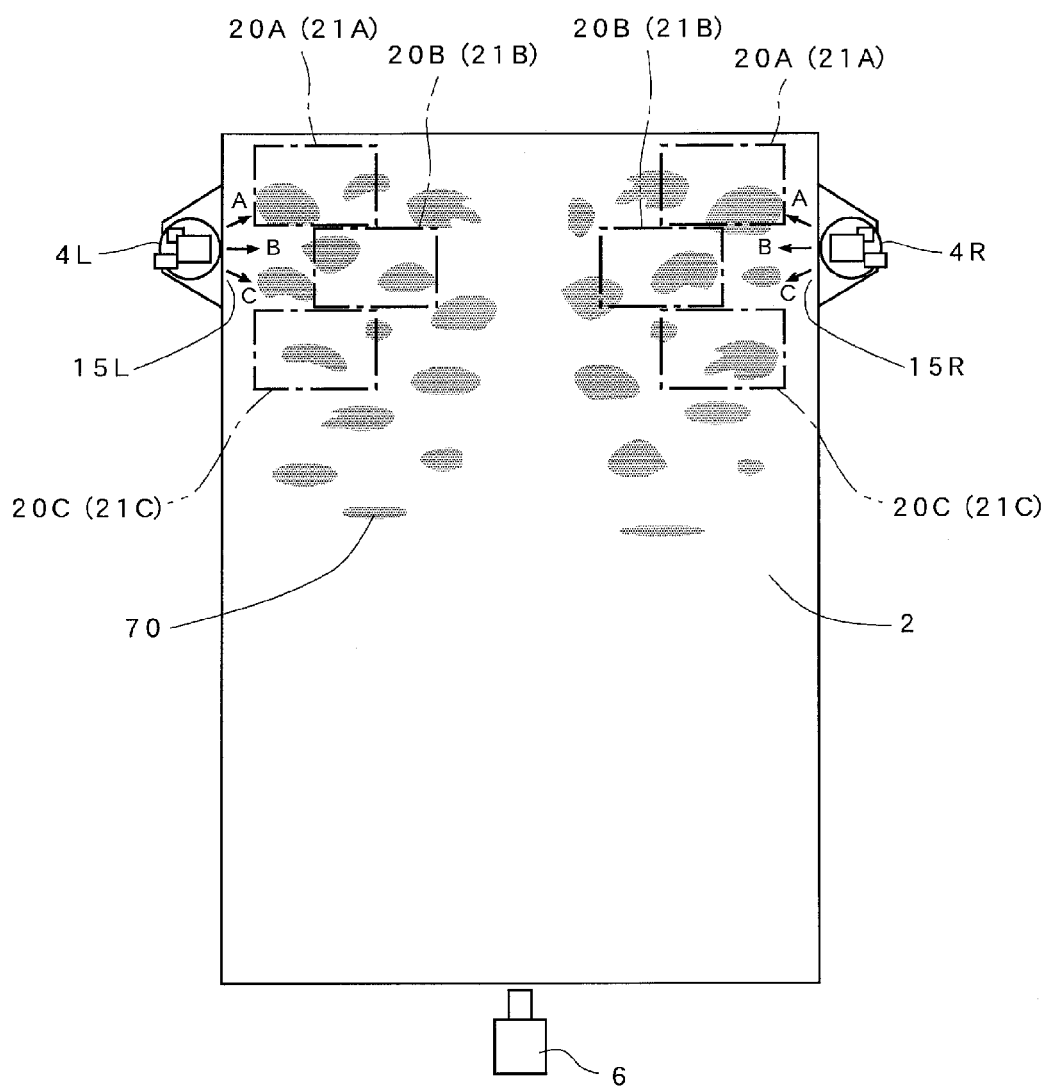
FIG. 8 is an explanatory diagram showing other monitored regions on a liquid surface of a melting bath and other regions to be measured on an image in an overlapping manner.

FIGS. 7 and 8 show a state of the liquid surface 7 of the molten glass filled in the melting bath 2. In these figures, portions shown by dots are unmolten glass batches 70 floating or exposed on the liquid surface 7. The unmolten glass batches 70 are widely distributed in the upstream region where the batch charging ports 15L and 15R are positioned, and the distribution amount thereof is reduced toward the downstream region.

The molten state of the glass batch charged into the melting bath 2 of the glass melting furnace 1 by the left and right batch chargers 4L and 4R is being monitored by using the image-capturing device 6 to observe the distribution state of the unmolten glass batches in a specified partial region. The image-capturing device 6 is placed above the downstream end of the melting bath 2, and the angle of view and direction of a lens thereof are set so as to contain the entire liquid surface 7 of the melting bath 2 within a viewing field thereof.

FIGS. 7 and 8 show specific examples of methods for monitoring a molten state of the glass batch charged into the melting bath 2 and methods for controlling the charging amount of the glass batch.

As shown in FIG. 7, according to a first method, a pair of left and right monitored regions 20L and 20R having the same rectangular shape and the same size are set side by side along a width direction at horizontally symmetrical positions in the upstream region of the melting bath 2, and it is determined whether the quality of the molten state of the charged glass batch is favorable or not and whether the amounts of the glass batch charged into the melting bath 2 by the batch chargers 4L and 4R are appropriate or not on the basis of how much of the unmolten glass batches 70 are unevenly distributed in which one of the monitored regions 20L and 20R. Note that the sizes of the monitored regions 20L and 20R do not always have to be the same.

Specifically, regions 21L and 21R to be measured, corresponding to the monitored regions 20L and 20R, are set on an image of the liquid surface 7 of the melting bath 2 obtained by the image-capturing device 6. Assuming that the areas of the regions 21L and 21R to be measured are equal to $SL_0$ and $SR_0$, respectively (in this embodiment, $SL_0=SR_0$), the total areas $S_L$ and $S_R$ of the image portions representing the unmolten glass batches 70 included in the respective regions 21L and 21R to be measured (hereinafter simply referred to as "batch image portions") are measured respectively, and then, the occupying ratios $k_L$ ($=S_L\times 100/SL_0$) and $k_R$ ($=S_R\times 100/SR_0$) of the total areas $S_L$ and $S_R$ of the batch image portions with respect to the areas $SL_0$ and $SR_0$ are then calculated respectively. Further, a difference $\Delta k$ ($=k_L-k_R$) between the occupying ratios is calculated.

Next, the calculated value of the difference $\Delta k$ between the occupying ratios is compared with predetermined positive and negative thresholds TH. If $\Delta k>TH$, the amount of the glass batch to be charged into the melting bath 2 from one batch charger 4L is reduced while increasing the amount of the glass batch to be charged into the melting bath 2 from the other batch charger 4R. In this manner, the ratio of the charging amounts is changed so as to achieve the same distributions of the unmolten glass batches 70 and thereby correct unevenness therebetween.

If the result of the comparison turns out to be $\Delta k<-TH$, the amount of the glass batch to be charged into the melting bath 2 from one batch charger 4L is increased while reducing the amount of the glass batch to be charged into the melting bath 2 from the other batch charger 4R. In this manner, the ratio of the charging amounts is changed so as to achieve the same distributions of the unmolten glass batches 70 and thereby correct unevenness therebetween.

In this embodiment, in order to increase or decrease the amount of the glass batch to be charged into the melting bath 2 by each of the batch chargers 4L and 4R, the number of rotations in the pusher motor 54 of each of the batch chargers 4L and 4R is changed so as to change the reciprocation speed of the pusher 50 thereof. However, the number of frequencies in the electromagnetic feeder 43 in each of the batch chargers 4L and 4R may be changed alternatively.

Note that the height of the liquid surface in the melting bath 2 is kept constant by adjusting the total charging amount of the glass batch made by both of the batch chargers 4L and 4R on the basis of detection signals from the liquid surface sensor S2 to be described later.

As shown in FIG. 8, according to a second method, three monitored regions 20A, 20B, and 20C having the same rectangular shape are set side by side along a longitudinal direction of the melting bath 2 in the respective batch charging directions A, B, and C employed by each of the batch chargers 4L and 4R in each of the vicinities of the batch charging ports 15L and 15R in the upstream region of the melting bath 2. It is then determined whether the quality of the molten state of the charged glass batch is favorable or not and whether the charging amounts (distribution amounts) of the glass batch charged into the melting bath 2 in the respective batch charging directions A to C by the respective batch chargers 4L and 4R are appropriate or not on the basis of how much of the unmolten glass batches 70 are distributed in the monitored regions 20A and 20C placed at the both ends.

Although the monitored regions 20A and 20C placed at the both ends are set to have the same size in this embodiment, they may have different sizes. Further, although the distribution states of the unmolten glass batches at the monitored regions 20A and 20C placed at the both ends from among the three monitored regions 20A, 20B, and 20C are obtained in the illustrated example, the distribution states of the unmolten glass batches may be obtained at two monitored regions with a different combination or the distribution state of the unmolten glass batches may be obtained at any one of the monitored regions.

Also in the embodiment shown in FIG. 6, monitored regions having the same rectangular shape are set side by side along a width direction of the melting bath 2 in the batch charging directions employed by the plurality of batch chargers 4A to 4D, respectively. Then, it is determined whether the quality of the molten state of the charged glass batch is favorable or not and whether the charging amounts (distribution amounts) of the glass batch charged into the respective monitored regions in the melting bath 2 by the batch chargers 4A to 4D are appropriate or not on the basis of how much of the unmolten glass batches 70 are distributed in predetermined one or more of the monitored regions.

Note that the monitored region based on which whether the distribution state of the glass batch is appropriate or not is determined may be fixed to any one of a plurality of monitored regions, or it may be changed sequentially.

In the specific example of FIG. 8, regions 21A and 21C to be measured, corresponding to the monitored regions 20A and 20C above, are set on the image of the liquid surface 7 in the melting bath 2 obtained by the image-capturing device 6. Assuming that the areas of the regions 21A and 21C to be measured are equal to $SA_0$ and $SC_0$, respectively (in this embodiment, $SA_0 = SC_0$), the total areas $S_A$ and $S_C$ of the batch image portions included in the respective regions 21A and 21C to be measured are measured respectively, and the occupying ratios $k_A$ (=$S_A \times 100/SA_0$) and $k_C$ (=$S_C \times 100/SC_0$) of the total areas $S_A$ and $S_C$ of the batch image portions with respect to the areas $SA_0$ and $SC_0$ are then calculated, respectively.

Next, the calculated value of one of the occupying ratios, $k_A$, is compared with predetermined thresholds TH1 and TH2 (where TH2<TH1). If $k_A$>TH1, the amount of the glass batch to be charged in the batch charging direction A from each of the batch chargers 4L and 4R is reduced. If $k_A$<TH2, the amount of the glass batch to be charged into the melting bath 2 in the batch charging direction A from each of the batch chargers 4L and 4R is increased. In this manner, the time length of the batch charging period $T_A$ for the batch charging direction A is controlled so that the occupying ratio $k_A$ is a value which falls within a certain range.

Similarly, the calculated value of the other occupying ratio $k_C$ is compared with predetermined thresholds TH3 and TH4 (where TH4<TH3). If $k_C$>TH3, the amount of the glass batch to be charged in the batch charging direction C from each of the batch chargers 4L and 4R is reduced. If $k_C$<TH4, the amount of the glass batch to be charged in the batch charging direction C from each of the batch chargers 4L and 4R is increased. In this manner, the time length of the batch charging period $T_C$ for the batch charging direction C is controlled so that the occupying ratio $k_C$ is a value which falls within a certain range.

Note that when the sum of the batch charging periods $T_A$ and $T_C$ ($T_A+T_C$) is changed, the batch charging period $2T_B$ for the batch charging direction B is correspondingly adjusted to $T-(T_A+T_C)$.

In the embodiment shown in FIG. 6, for any one of the batch chargers, the occupying ratio of the total area of the batch image portions within the region to be measured is calculated, and the number of rotations of the screw thereof is changed on the basis of a comparison result between the calculated value and a predetermined threshold so as to increase or decrease the charging amount (distribution amount) of the glass batch. For the other batch chargers, the numbers of rotations of the screws thereof are uniformly adjusted to change the charging amounts (distribution amounts) of the glass batch.

As shown in FIG. 7, according to a third method, a monitored region 20D is set in the downstream region of the melting bath 2, and it is determined whether the quality of the molten state of the charged glass batch is favorable or not on the basis of how much of the unmolten glass batches 70 are traveled down to the monitored region 20D in the downstream region from the upstream region.

Specifically, a region 21D to be measured, corresponding to the monitored region 20D above, is set on the image of the liquid surface 7 in the melting bath 2 obtained by the image-capturing device 6. Assuming that the area of the region 21D to be measured is equal to $SD_0$, the total area $S_D$ of the batch image portions included in the region 21D to be measured is measured, and then the occupying ratio $k_D$ (=$S_D \times 100/SD_0$) of the total area $S_D$ of the batch image portions with respect to the area $SD_0$ is then calculated.

Next, the calculated value of the occupying ratio $k_D$ is compared with a predetermined threshold TH5. If $k_D$>TH5, an alarm 9 not shown in this figure (shown in the block diagram of FIG. 10) is actuated so as to urge an operator to take a countermeasure such as an adjustment of the burning capacity of the combustion burners 3L and 3R. If the condition of $k_D \leq$ TH5 is achieved, the actuation of the alarm 9 is stopped.

Figure 9:
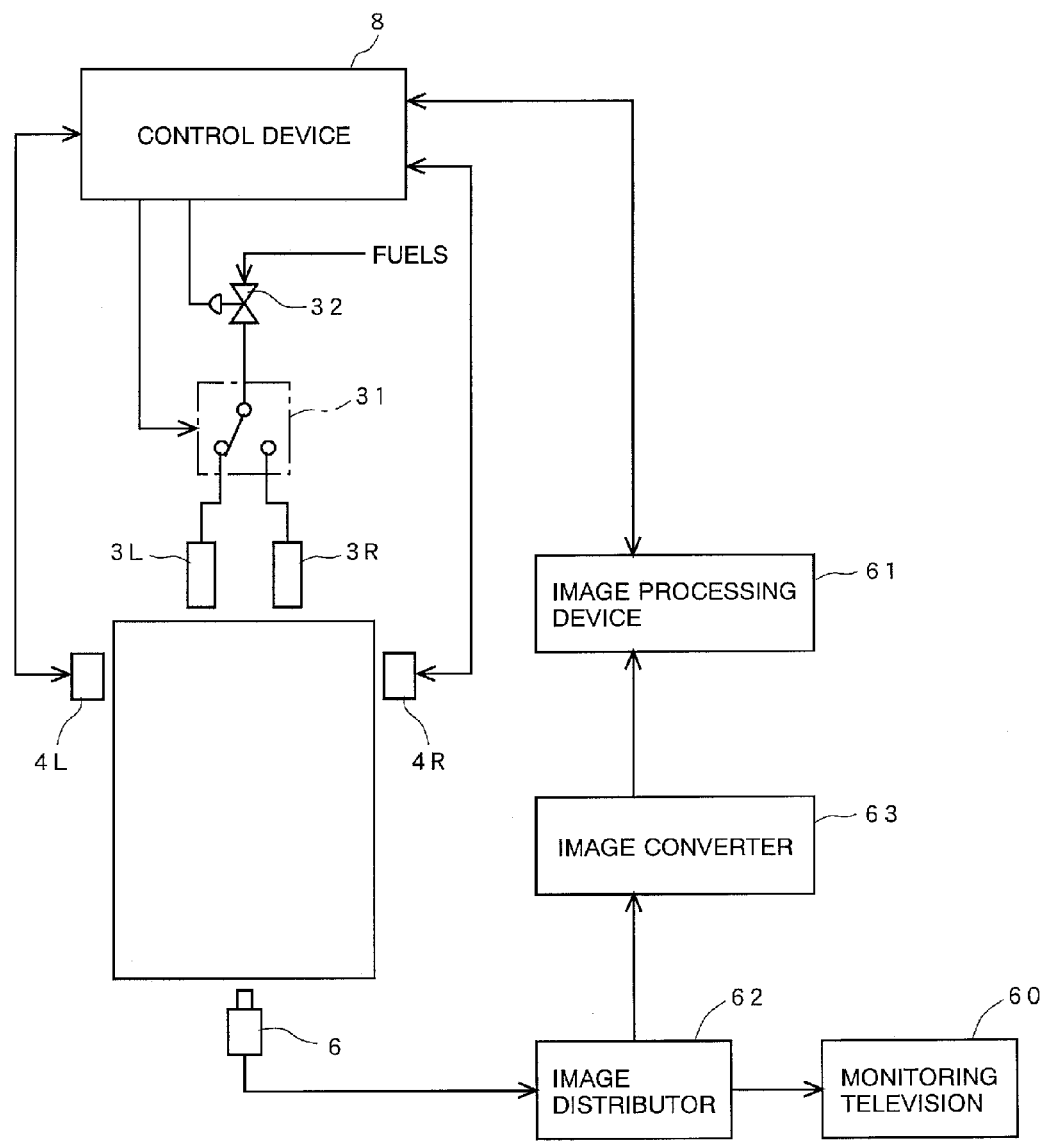
FIG. 9 is an explanatory diagram showing the outline of a control system of a glass melting furnace.

FIG. 9 shows a general configuration of a control system for controlling the charging and heating operations of the glass batch in the glass melting furnace 1 described above.

In this figure, reference numeral 31 denotes a change-over switch used to supply fuels to the left and right combustion burners 3L and 3R in an alternate manner for combustion. Reference numeral 32 denotes a control valve used to control the supply of the fuels to the change-over switch 31. The switching operation of the change-over switch 31 and the opening and closing operations of the control valve 32 are controlled by a control device 8.

The image-capturing device 6 described above is formed by a color television camera, for example, and NTSC video signals are sent from the image-capturing device 6 to the monitoring television 60 through an image distributor 62. The state of the liquid surface 7 in the melting bath 2, which is changing momentarily, is displayed on the monitoring television 60 with color images. The video signals are distributed to an image converter 63 by the image distributor 62. The image converter 63 converts the color video into color still images compressed in a JPEG format or the like, and supplies the color still images to the image processing device 61.

The image processing device 61 downloads the color still images from the image converter 63, and performs an image processing thereto according to anyone of the first to third methods described above. After measuring the total area of the batch image portions included in the region to be measured and the occupying ratio thereof, the image processing device 16 determines whether the quality of the molten state of the glass batch is favorable or not on the basis of the measured values and whether the amounts of the glass batch charged into the melting bath 2 from the batch chargers 4L and 4R are appropriate or not. The determination results are provided to the control device 8, and the control device 8 outputs, to the respective batch chargers 4L and 4R, control signals to increase or decrease the amounts of the glass batch to be charged into the melting bath 2 from the batch chargers 4L and 4R on the basis of the determination result according to the first or second method.

Figure 10:
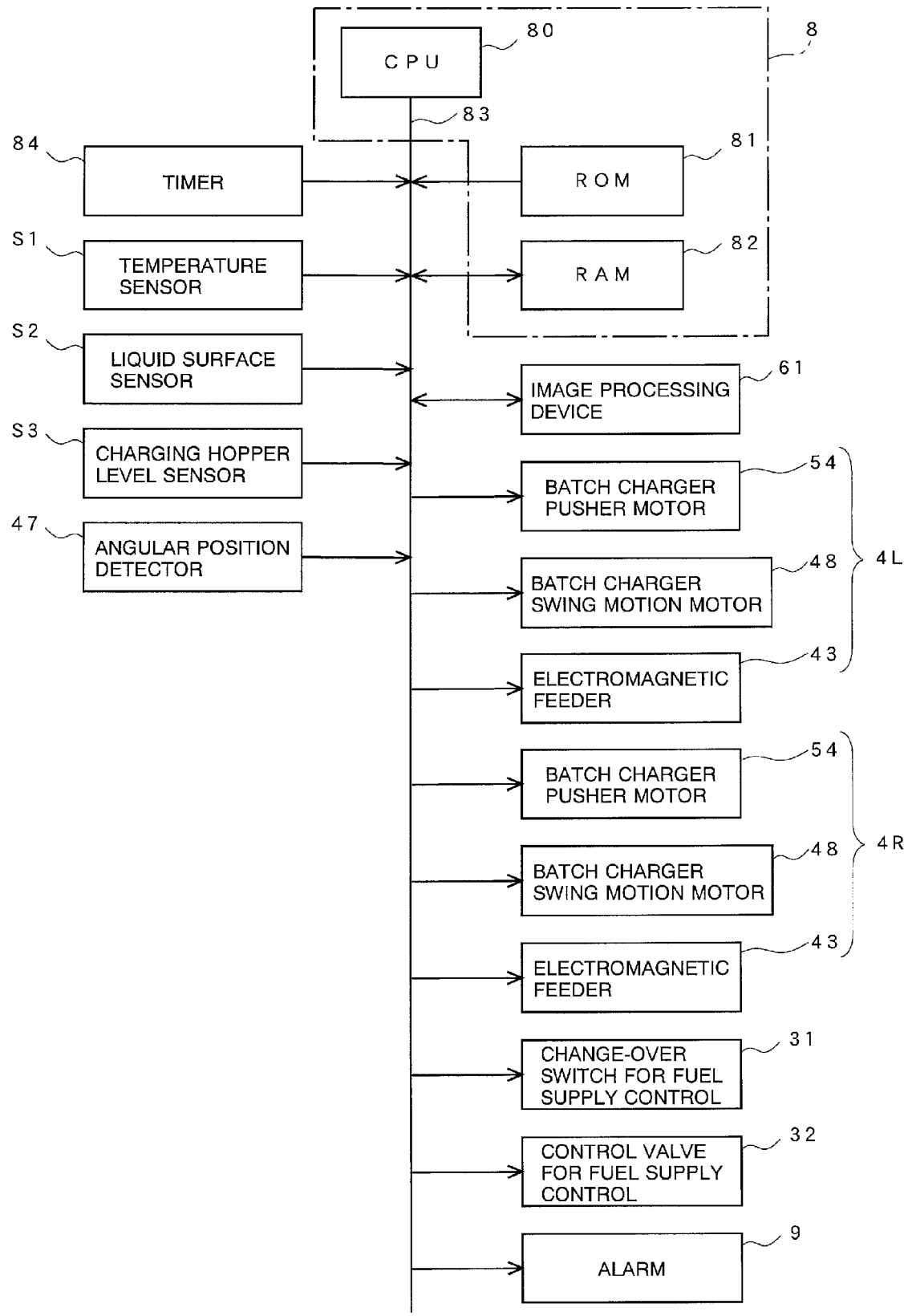
FIG. 10 is a block diagram showing the configuration of a control device.

The control device 8 is formed by a microcomputer, and includes a CPU 80 to perform a predominant role in control and computing, a ROM 81 for storing a program and fixed data, a RAM 82 for storing various data, and the like as shown in FIG. 10. Connected to the CPU 80 via a bus 83 are output sections such as the image processing device 61, the pusher motors 54, swing motion motors 48, and electromagnetic feeders 43 of the left and right batch chargers 4L and 4R, the change-over switch 31 and the control valve 32 for controlling fuel supply, and the alarm 9, and input sections such as the timer 84, a temperature sensor S1, the liquid surface sensor S2, a level sensor S3, and the angular position detector 47. The CPU 80 executes the program stored in the ROM 81 and controls a series of input and output operations for the respective input and output sections while writing and reading data to and from the RAM 82.

In the above-described configuration shown in FIG. 10, the electromagnetic feeder 43 is to resupply the glass batch to the hopper 44 when the level sensor S3 detects that the amount of the glass batch retained in the hopper 44 in each of the batch chargers 4L and 4R has decreased below the set amount. Once the glass batch is resupplied up to the set level, the resupply operation of the electromagnetic feeder 43 is stopped. The alarm 9 is actuated when the unmolten glass batches 70 in an amount greater than the set amount are traveled down to the monitored region 20D in the downstream region of the melting bath 2 so as to notify an operator of the situation. The timer 84 times the passages of the swing motion stop periods $T_A$ to $T_C$ in each of the batch chargers 4L and 4R. The temperature sensor S1 measures the temperature in the melting section 10 of the glass melting furnace 1 in order to adjust the temperature in the furnace. The liquid surface sensor S2 is to output a detection signal according to the height of the liquid surface and is placed in the clarifying section 11 described above. The total charging amount of the glass batch is controlled on the basis of the detection signal from the liquid surface sensor S2 so that the liquid surface 7 of the melting bath 2 is kept at a constant height.

The image processing device 61 described above is also formed by a microcomputer, and includes a CPU to perform a predominant role in control and computing, a ROM for storing a program and fixed data, and a RAM used for the writing and reading of data.

Figure 11:
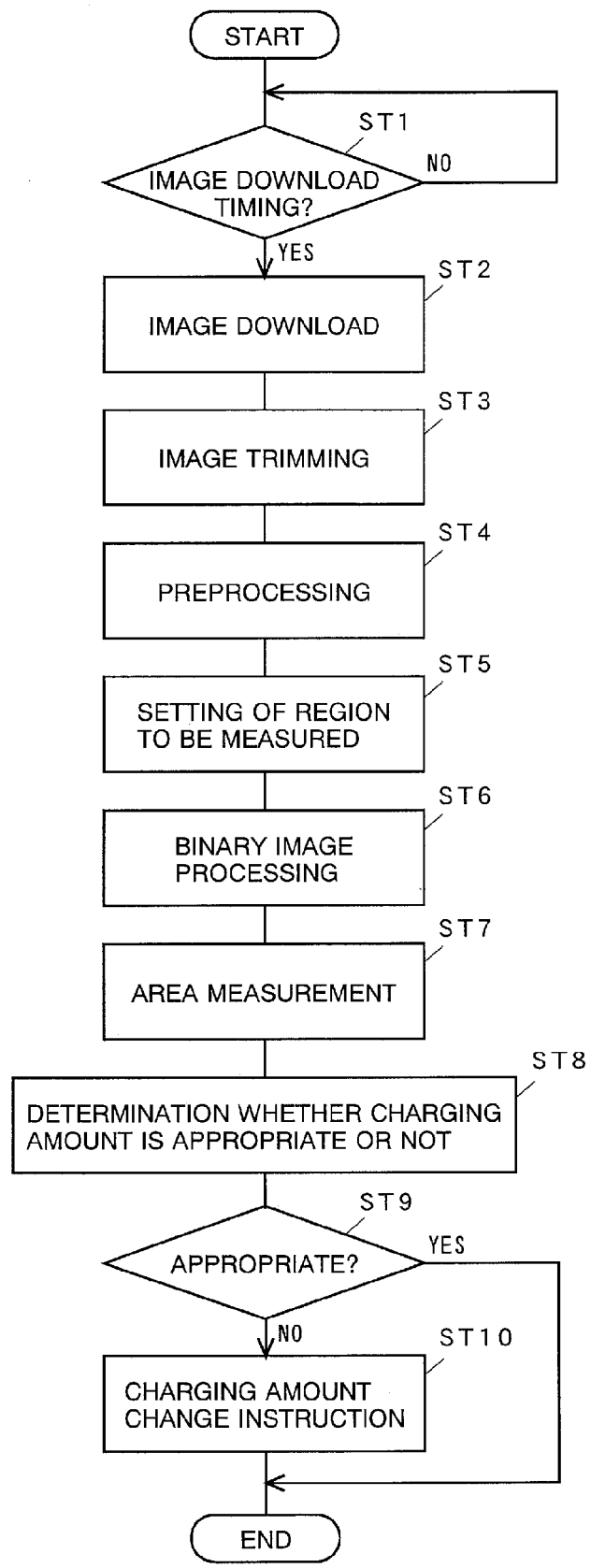
FIG. 11 is a flow chart showing a control flow of an image processing device.

The CPU of the image processing device 61 sequentially executes steps (denoted as "ST" in the figure) shown in FIG. 11 in accordance with the program stored in the ROM to determine whether the amounts of the glass batch charged by the left and right batch chargers 4L and 4R are appropriate or not. If it is determined that the charging amounts are not appropriate, the CPU of the image processing device 61 instructs the control device 8 to change the charging amounts of the glass batch by an increase or decrease thereof.

Next, the steps of FIG. 11 will be described. In ST1, the CPU of the image processing device 61 is on standby for the download of images. At the image download timing, the determination in ST1 is changed to "YES" and the step proceeds to ST2 where the color still images are downloaded from the image converter 63. Then, the step proceeds to an image processing step to be described below.

Figure 12:
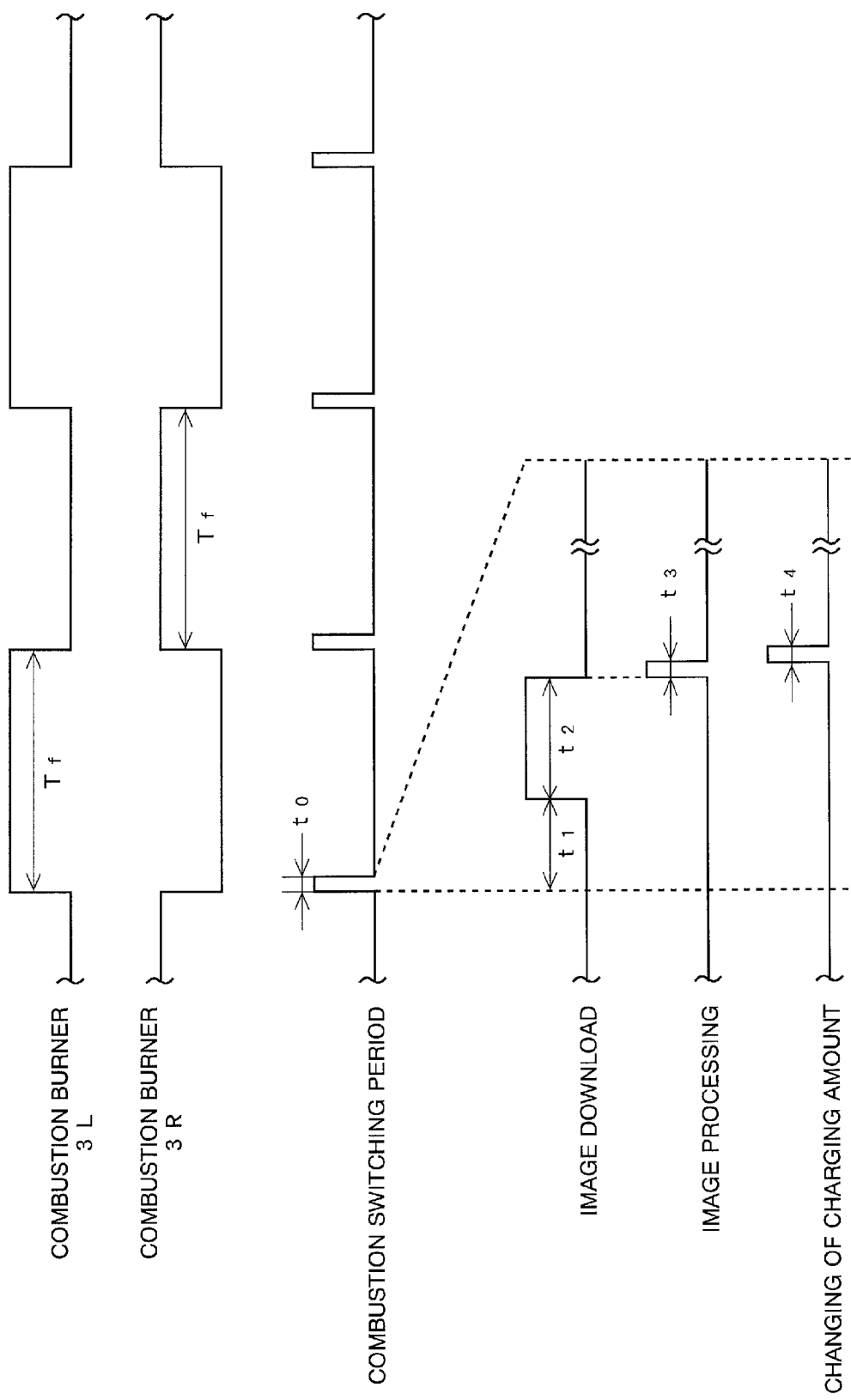
FIG. 12 is a timing chart showing image download timing.
Figure 13:
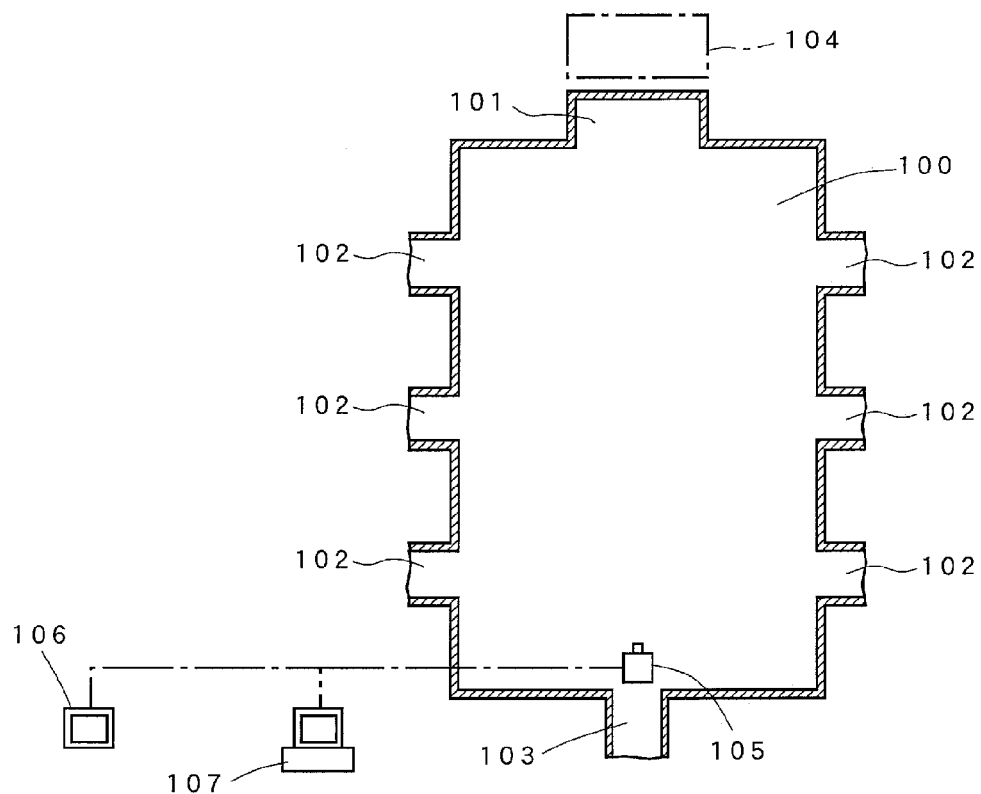
FIG. 13 is a horizontal cross-sectional view showing the configuration of a melting bath in a conventional glass melting furnace.
Figure 14:
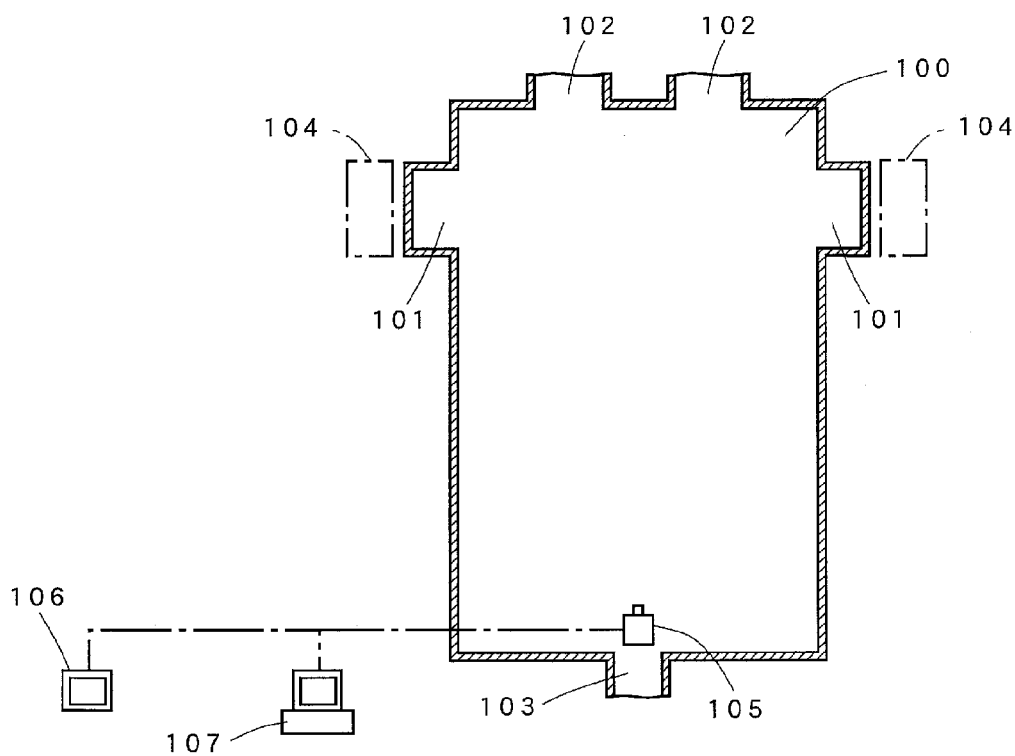
FIG. 14 is a horizontal cross-sectional view showing the configuration of a melting bath in another conventional glass melting furnace.

The image download timing in the image processing device 61 corresponds to a timing at which the flame f of the combustion burners 3L and 3R disappears and a good visibility for the image-capturing device 6 is thereby obtained, i.e., a timing at which a combustion operation of the combustion burners 3L and 3R is switched to another as shown in FIG. 12.

Each of the combustion burners 3L and 3R repeats a combustion operation and a combustion stop operation in an alternate manner at regular time intervals $T_f$. A combustion switching period $t_0$ during which the switching therebetween is performed is allocated to periods t2, t3, and t4 during which processes for the image downloading, the image processing, and the change of the charging amounts are performed. Note that in this figure, t1 represents a period required for the flame to disappear from the glass melting furnace 1 after the combustion operation of the combustion burners 3L and 3R is stopped. During the following predetermined period t2, a plurality of images are downloaded into the image processing device 61 at regular time intervals.

Returning now to FIG. 11, after the plurality of images are downloaded in ST2, image portions to be subjected to an image processing are trimmed and unnecessary image portions are removed in the following ST3. In the following preprocessing step in ST4, each color image is first changed to a monochrome image, and the plurality of downloaded images are overlaid on one another so as to obtain one sample image in which the concentration of each pixel is averaged for the purpose of noise removal. This sample image is an image obtained when the liquid surface 7 of the molten glass in the melting bath 2 is viewed downwardly from an obliquely upward position. Thus, a correction process for correcting such an image to an image as viewed downwardly from a position directly above is executed, and an image to be measured is thus obtained.

After the above-described preprocessing step in ST4 is completed, the process proceeds to the following ST5. In ST5, the above-described regions to be measured, i.e., the regions 21L and 21R to be measured shown in FIG. 7 in a case where the first method is implemented, or the regions 21A and 21C to be measured shown in FIG. 8 in a case where the second method is implemented, or the region 21D to be measured shown in FIG. 7 in a case where the third method is implemented, are set in the image to be measured. Thereafter, the image within the region to be measured is subjected to a binarization process so as to convert a grayscale image to a binary image (ST6).

In the following ST7, the total area of the batch image portions included in the region to be measured is measured.

This area measurement is achieved for example by counting the number of pixels (black pixels, for example) forming the batch image portions from among black and white pixels forming the binary image. After the area measurement in ST7, the occupying ratio of the total area of the batch image portions with respect to the area of the region to be measured is calculated, and it is determined whether the amount of the glass batch charged by each of the batch chargers 4L and 4R is appropriate or not in the following ST8. If it is determined that the charging amounts are not appropriate as a result of the determination, the determination in the following ST9 will be "NO" and the process proceeds to ST10 where the control device 8 is instructed to change the charging amounts by an increase or decrease thereof.

REFERENCE SIGNS LIST 1 glass melting furnace
2, 100 melting bath
4L, 4R, 4A to 4D batch charger
6 image-capturing device
7 liquid surface
8 control device
61 image processing device
70 unmolten glass batch

The invention claimed is:

1. A glass melting furnace batch charging control device for controlling a charging amount of glass batch material on the basis of a molten state of glass batch material charged into a melting bath of a glass melting furnace by a first batch charger and a second batch charger, the molten state being determined on the basis of a distribution state of unmolten glass batch material in a first partial region of the melting bath that is disposed adjacent the first batch charger and in a second batch charger that is disposed adjacent the second batch charger, the device comprising:
    image-capturing means for capturing an image of a liquid surface of the melting bath from a position above the melting bath;
    area measuring means for setting first and second regions to be measured in an image obtained by the image-capturing means, the first region to be measured lying in the first partial region and the second region to be measured lying in the second partial region, and for measuring occupying ratios of areas occupied by unmolten glass batch material in the first and second regions to be measured;
    determination means for recognizing a distribution state of the unmolten glass batch material in the first and second partial regions from measured values obtained by the area measuring means, and for determining whether a quality of the molten state of the glass batch material is favorable or not; and
    control means for controlling an amount of glass batch material to be charged into the melting bath by the first and second batch chargers on the basis of the determination result made by the determination means.

2. The glass melting furnace batch charging control device according to claim 1, wherein:
    the first and second batch chargers are provided at horizontally symmetrical positions on both sides of an upstream region of the melting bath;
    the area measuring means sets the first and second regions to be measured at horizontally symmetrical positions in a region corresponding to the upstream region on the image, and measures respective occupying ratios of areas occupied by image portions representing unmolten glass batch material in the regions to be measured; and
    the determination means recognizes distribution states of the unmolten glass batch material in the first and second partial regions from differences between measured values obtained by the area measuring means, and determines whether the quality of the molten state of glass batch material is favorable or not.

3. The glass melting furnace batch charging control device according to claim 2, wherein:
    the determination means compares differences between the occupying ratios of the areas occupied by the image portions representing unmolten glass batch material in the first and second regions to be measured with a threshold to recognize the distribution states of the unmolten glass batch material in the first and second partial regions and thereby determine whether the quality of the molten state of glass batch material is favorable or not; and
    the control means changes a ratio of the charging amounts of glass batch material by the first and second batch chargers when the determination means makes a determination that the quality of the molten state is not favorable.

4. The glass melting furnace batch charging control device according to claim 1, wherein:
    at least one further first region to be measured lies in the first partial region and at least one further second region to be measured lies in the second partial region;
    the area measuring means measures occupying ratios of any one of the first regions to be measured and any one of the second regions to be measured; and
    and the determination means recognizes a distribution state of the unmolten glass batch material from measured values obtained by the area measuring means, and determines whether the quality of the molten state of the glass batch material is favorable or not.

5. The glass melting furnace batch charging control device according to claim 4, wherein:
    the determination means compares the occupying ratio of the unmolten glass batch material in the first and second regions to be measured with a threshold to recognize the distribution state of the glass batch material in the partial regions and thereby determine whether the quality of the molten state of the glass batch material is favorable or not; and
    the control means controls the amount of the glass batch material to be charged into each of the partial regions by the first and second batch chargers when the determination means makes a determination that the quality of the molten state is not favorable.

6. A batch charging control device for use with a glass melting furnace having first and second ends and left and right sides, a left batch charger being disposed at the left side adjacent the first end to introduce glass batch material to a left interior region of the furnace and a right batch charger being disposed at the right side adjacent the first and to introduce glass batch material to a right interior region of the furnace, said control device comprising:
    image-capturing means, disposed adjacent the second end of the furnace, for capturing images of the left and right interior regions of the furnace;
    measuring means for measuring left and right occupying ratios of areas occupied by unmolten glass batch material in predetermined portions of the images of the left and right interior regions;

determination means for determining whether the left and right occupying ratios satisfy at least one predetermined criterion; and control means for controlling the left and right glass batch chargers in response to the determination means.

7. The control device of claim 6, wherein the at least one predetermined criterion includes whether the difference between the left occupying ratio and the right occupying ratio exceeds a predetermined threshold value.

8. The control device of claim 6, wherein the at least one predetermined criterion includes whether the left occupying ratio is greater than a first predetermined ratio or smaller than a second predetermined ratio, and also whether the right occupying ratio is greater than a third predetermined ratio or smaller than a fourth predetermined ratio.

* * * * *